(12) United States Patent
Zeller

(10) Patent No.: US 11,898,036 B2
(45) Date of Patent: Feb. 13, 2024

(54) ELASTOMER COMPOSITE INCLUDING ALGAE BIOMASS FILLER

(71) Applicant: ALGIX, LLC, Meridian, MS (US)

(72) Inventor: Mark Ashton Zeller, Meridian, MS (US)

(73) Assignee: ALGIX, LLC, Meridian, MS (US)

( * ) Notice: Subject to any disclaimer, the term of this patent is extended or adjusted under 35 U.S.C. 154(b) by 1224 days.

(21) Appl. No.: 16/396,370

(22) Filed: Apr. 26, 2019

(65) Prior Publication Data

US 2019/0330453 A1 Oct. 31, 2019
US 2021/0261761 A9 Aug. 26, 2021

Related U.S. Application Data

(60) Provisional application No. 62/663,893, filed on Apr. 27, 2018.

(51) Int. Cl.

| | | |
|---|---|---|
| C08L 9/06 | (2006.01) | |
| G06F 16/27 | (2019.01) | |
| G06F 16/23 | (2019.01) | |
| B29C 70/58 | (2006.01) | |
| B29D 35/00 | (2010.01) | |
| B29D 35/06 | (2010.01) | |
| B29D 35/12 | (2010.01) | |
| C08L 7/00 | (2006.01) | |
| C08L 9/02 | (2006.01) | |
| C08L 11/00 | (2006.01) | |
| C08L 15/00 | (2006.01) | |
| C08L 19/00 | (2006.01) | |
| C08L 23/16 | (2006.01) | |
| C08L 23/28 | (2006.01) | |
| C12N 1/12 | (2006.01) | |
| G06F 21/60 | (2013.01) | |
| H04L 9/32 | (2006.01) | |
| H04L 67/10 | (2022.01) | |
| B29K 9/06 | (2006.01) | |
| B29K 19/00 | (2006.01) | |
| C08K 5/00 | (2006.01) | |
| C08K 5/07 | (2006.01) | |
| C08K 5/14 | (2006.01) | |

(Continued)

(52) U.S. Cl.
CPC ............... *C08L 9/06* (2013.01); *B29C 70/58* (2013.01); *B29D 35/0054* (2013.01); *B29D 35/065* (2013.01); *B29D 35/122* (2013.01); *C08L 7/00* (2013.01); *C08L 9/02* (2013.01); *C08L 11/00* (2013.01); *C08L 15/005* (2013.01); *C08L 19/00* (2013.01); *C08L 23/16* (2013.01); *C08L 23/286* (2013.01); *C12N 1/12* (2013.01); *G06F 16/2379* (2019.01); *G06F 16/27* (2019.01); *G06F 21/602* (2013.01); *H04L 9/3239* (2013.01); *H04L 67/10* (2013.01); *B29K 2009/06* (2013.01); *B29K 2011/00* (2013.01); *B29K 2019/00* (2013.01); *C08K 5/0016* (2013.01); *C08K 5/0025* (2013.01); *C08K 5/07* (2013.01); *C08K 5/14* (2013.01); *C08K 5/29* (2013.01); *H04L 9/50* (2022.05)

(58) Field of Classification Search
CPC ..... C12N 1/12; C08L 9/02; C08L 9/06; C08L 11/00; C08L 15/00; C08L 19/00; C08L 7/00; C08L 15/005; C08L 23/16; C08L 23/286; B29C 70/58; B29D 35/0054; B29D 35/065; B29D 35/122; G06F 16/2379; G06F 16/27; G06F 21/602; H04L 9/3239; H04L 67/10; H04L 9/50; B29K 2009/06; B29K 2011/00; B29K 2019/00; C08K 5/0016; C08K 5/0025; C08K 5/07; C08K 5/14; C08K 5/29
See application file for complete search history.

(56) References Cited

U.S. PATENT DOCUMENTS

| | | |
|---|---|---|
| 5,352,709 A | 4/1994 | Tarrant et al. |
| 9,574,066 B1 | 2/2017 | Du et al. |

(Continued)

FOREIGN PATENT DOCUMENTS

KR  101182251 B1 * 9/2012

OTHER PUBLICATIONS

English-language machine translation of KR101182251-B1, performed on Espacenet on Jun. 29, 2022, 19 pages.*

(Continued)

*Primary Examiner* — Angela C Scott
(74) *Attorney, Agent, or Firm* — Foster Swift Collins & Smith PC; Mikhail Murshak

(57) ABSTRACT

An algae-elastomer composite including an elastomer matrix; algae; and a mixing additive sufficient to achieve a desired property. The algae can be present in a milled condition having a particle size value of between about 10 and 120 microns. The algae is mixed with the elastomer matrix in a dry condition having a moisture content of below about 10%. A method of preparing the algae-based elastomer composite is provided that includes the steps of: pre-mixing an elastomer matrix; adding an algae filler; adding a mixing additive that includes a plasticizer; forming an elastomer-algae blend by blending the algae and elastomer to a temperature sufficient to be further mixed, wherein the temperature is about 10° C. higher than the temperature sufficient for the elastomer alone; adding and mixing a curing or vulcanizing agent for the elastomer dispersing the elastomer-algae blend; and heating and curing the elastomer-algae blend into a final form.

16 Claims, 6 Drawing Sheets

(51) Int. Cl.
C08K 5/29 (2006.01)
H04L 9/00 (2022.01)

(56) References Cited

U.S. PATENT DOCUMENTS

| | | |
|---|---|---|
| 10,077,454 B1* | 9/2018 | Davis .................... C12P 7/065 |
| 2010/0272940 A1 | 10/2010 | Shi et al. |
| 2011/0178233 A1 | 7/2011 | Chaboche et al. |
| 2017/0183469 A1* | 6/2017 | Falken ..................... C08J 3/22 |
| 2018/0057687 A1 | 3/2018 | Shi et al. |
| 2018/0000137 A1 | 4/2018 | Freres |

OTHER PUBLICATIONS

Fatima Zia et al., "Algae-Based Polyurethane Blends and Composites," Chapter 11 in Algae Based Polymers, Blends, and Composites, 415-458 (2017).*
International Search Report, dated Jul. 30, 2018 for PCT/US2019/029461, 13 pages.

* cited by examiner

| Item 10 | Test result |
|---|---|
| Content | 30% masterbatch 70% elastomer (NBR) |
| Algae percentage | 15% |
| S.G. | 1.15 |
| Tear | 7.45 |
| Split tear | 14 |
| Din abrasion | 146 |
| Hardness | 58-60 ASKER A |
| Elongation | 46 |

| Item 30 | | |
|---|---|---|
| Physical Property | Test Method | 10% Algae |
| Durometer (Shore A) | ASTM D-2240 | 62+/-3A |
| Tensile (kg/cm$^2$) | ASTM D-412 | 80 |
| Elongation (%) | ASTM D-412 | 400 |
| Die C Tear (kg/cm) | ASTM D-624 | 30 |
| Density (g/cc) | ASTM D-297 | 1.15+/-0.03 |
| Abrasion (DIN) | DIN 53516 | 80 |

FIG. 2C

| Test items | test result- 10% algae | test result- 5% algae |
|---|---|---|
| Hardness (Shore A) | 61 | 60 |
| SG (g/cm$^3$) | 1.11 | 1.09 |
| Tensile (kg/cm) | 93 | 112 |
| Elongation (%) | 403% | 618% |
| Tear (kg/cm) | 66 | 69 |
| DIN (mm$^3$) | 80 | 65 |
| Dry slip | 0.86/1.02/1.03 | 1.18 |
| Wet slip | 0.25/ 0.27/ 0.31 | 0.31 |

FIG. 2D

Density

The density ranged from 5.9 to 6.6 pounds/cubic feet for the samples. The higher density could be attributed to higher state for cure.

The thickness ranged from 0.953 to 1.1013 inches for the samples. The thiner thickness could be attributed to higher state for cure.

ELASTOMER COMPOSITE INCLUDING ALGAE BIOMASS FILLER

CROSS REFERENCE TO RELATED APPLICATION

This Application claims priority to and the benefit of U.S. Provisional Patent Application No. 62/663,893, titled "ELASTOMER COMPOSITE INCLUDING ALGAE BIOMASS FILLER," and filed on Apr. 27, 2018, the disclosure of which is incorporated herein by reference in its entirety for all purposes.

TECHNICAL FIELD

The present disclosure relates generally to the field of elastomers and elastomer composite production using biomass.

DESCRIPTION OF RELATED ART

Rubber and elastomer composites are often desired for consumer goods, particularly for footwear, anti-fatigue mats, gasketing, insulation, sporting goods, automotive parts, and other related industries. An elastomer composite includes a filler material that may modify the elastomer to result in desired mechanical, thermal and other physical properties such as hardness, durability, strength, resilience, temperature stability, and the like. Moreover, there is an environmental incentive to identify reusable filler components to reduce the negative impact of using fossil fuels to manufacture products and in the case of algae to improve the trophic state of waters from which the algae is removed from with wide ranging ecological benefits.

U.S. Pat. No. 9,574,066 to Du et al. discloses a rubber composition comprised of at least one conjugated diene-based elastomer containing triglyceride based algae oil and to a tire with a component thereof.

Despite other attempts to solve the problems associated with a forming elastomer composites, none of these teach or suggest a material and/or method having the benefits and features of the present disclosure.

SUMMARY

The present disclosure provides for a biomass-elastomer composite including an elastomer matrix and a biomass reinforcement distributed through the elastomer matrix, wherein the biomass includes algae. The algae biomass may further include any additives sufficient to achieve a desired mixing and/or property. The biomass can further be provided directly as dry algae in particle form or in a masterbatch combined with a thermoplastic. The composite can be a solid composite or a foam composite.

The present disclosure provides for an algae-elastomer composite including: (a) an elastomer matrix; (b) a biomass reinforcement distributed through the elastomer matrix, wherein the biomass includes algae; and (c) a mixing additive sufficient to achieve a desired property. In an example, the algae is present in a milled condition having a mean particle size value of between up to about 120 microns. The algae can mixed with the elastomer matrix in a dry condition having a moisture content of below about 20%. In another example, the algae is mixed with the elastomer matrix in a dry condition having a moisture content of below about 3%. The elastomer matrix can be selected from the group consisting of Natural Rubber (NR), Butadiene Rubber (BR), Acrylonitrile Butadiene Rubber (NBR), Styrene Butadiene Rubber (SBR), Hydrogenated Acrylonitrile Butadiene Rubber (HNBR), Ethylene Propylene Diene Rubber (EPDM), Chloroprene Rubber (CR), Chlorinated Polyethylene Rubber (CM), Silicone Rubber (Q), and combinations thereof. The algae can be present in an amount of between about 1% to 75% by weight of composite. In yet a further example, the algae is selected from the group of algae species consisting of Haptophyta, Cyanophyta, Chlorophyta, Ochrophyta, Rhodophyta, Phaeophyta and combinations thereof.

Algae biomass typically includes protein, ash, carbohydrate, and lipids. In an example, the algae biomass includes a composition of protein from about 1% to 60%, ash from about 1% to 90%, carbohydrate from about 1% to 50%, and lipid from about 1% to 30%. The mixing additive can include plasticizers and performance enhancing additives operable to deliver the desired properties of the composite material. In yet another example, the elastomer is present in a premixed condition resulting in a plasticized state.

The composite of the present disclosure can further include an additive selected from the group consisting of an elastomer compound having polar functionalization, a thermoplastic compound having polar functionalization, a compatibilizer, a coupling agent, and combinations thereof. The elastomer compound having polar functionalization or the thermoplastic compound having polar functionalization can further include a functionalizing agent selected from the group consisting of a carboxylate, styrene, methyl methacrylate, acrylonitrile, glycidyl methacrylate, maleic anhydride, epoxide, and combinations thereof. In yet another example, the additive is a coupling agent having at least one member selected from the group consisting of isocyanate, peroxide, glyoxal coupling agents (XNBR) and combinations thereof. In still another example, the additive can be present in a premixed condition with the elastomer matrix.

The present disclosure provides for a shoe component including the algae-elastomer composite of and of the examples previously disclosed, wherein the shoe component is selected from the group consisting of an outsole, midsole, insole and combinations thereof.

The present disclosure further provides for a method of preparing an algae-based elastomer composite, the method including the steps of: (a) premixing an elastomer matrix in a mixer for a period of time sufficient to plasticize the elastomer into a suitable condition for mixing; (b) adding an algae filler into the mixer, wherein the algae filler is provided as particles; (c) blending the algae and elastomer to form an elastomer-algae blend, wherein the blend is heated to a temperature sufficient to be further mixed and wherein the temperature is about 10° C. higher than the temperature sufficient for the elastomer alone; (d) adding and mixing a curing or vulcanizing agent for the elastomer, wherein the amount of curing or vulcanizing agents are provided in an amount of about 10% to 500% more than sufficient to provide to cure or vulcanize an elastomer absent the algae; (e) dispersing the elastomer-algae blend; and (f) heating and curing the elastomer-algae blend into a final form. The method can further include the step of incorporating at least one additive selected from the group consisting of an elastomer compound having polar functionalization, a thermoplastic compound having polar functionalization, a compatibilizer, a coupling agent, and combinations thereof, to the premixing step (a) to enhance compatibility of the algae with the elastomer. In another example, the heating and curing step (f) includes extruding through an extruder to heat and mix the blend followed by passing through a heating tunnel to be cured and foamed into an elastomer-algae blend foam sheet. In yet a further example, the heating and curing step (f) forms flat sheets and includes the step of applying the flat sheets or pre-cut forms to a mold to press the blend into a desired form prior to the heating and curing step. In still yet another example, the desired form is a shoe component selected from the group consisting of as an outsole, midsole, insole or the like.

For purposes of summarizing the disclosure, certain aspects, advantages, and novel features of the disclosure have been described herein. It is to be understood that not necessarily all such advantages may be achieved in accordance with any one embodiment of the disclosure. Thus, the disclosure may be embodied or carried out in a manner that achieves or optimizes one advantage or group of advantages as taught herein without necessarily achieving other advantages as may be taught or suggested herein. The features of the disclosure which are believed to be novel are particularly pointed out and distinctly claimed in the concluding portion of the specification. These and other features, aspects, and advantages of the present disclosure will become better understood with reference to the following drawings and detailed description.

BRIEF DESCRIPTION OF THE DRAWINGS

The figures which accompany the written portion of this specification illustrate embodiments and method(s) of use for the present disclosure constructed and operative according to the teachings of the present disclosure.

FIG. 2C is a chart of test data for the final product 30 of FIG. 2A.

FIG. 2D is a comparison chart of a do different direct algae content elastomer final solid products.

The various embodiments of the present disclosure will hereinafter be described in conjunction with the appended drawings, wherein like designations denote like elements.

DETAILED DESCRIPTION

The present disclosure provides for a composition of matter and methods to produce sustainable elastomer composite materials using algae as a bio-based filler. Algae biomass and components of algae can be derived from both a microalgae and a macroalgae. Algae biomass includes but is not limited to biomass produced by algae species. Example algae species include, but are not limited to, Haptophyta, Cyanophyta, Chlorophyta, Ochrophyta, Rhodophyta, and Phaeophyta, for example blue-green algae, green algae, diatoms, red algae, and brown algae.

In one form, the algae biomass includes a composition of protein from about 1% to 60%, ash from about 1% to 90%, carbohydrates from about 1% to 50%, and lipids from about 1% to 30%. The algae biomass may be washed or fractionated to achieve better compositions for rubber incorporation, or they may be harvested with a composition which is well suited for elastomer incorporation. Due to interactions between protein and sulfur based curing or vulcanizing agents, a composition which is lower in protein can be desired since it will improve the processability of the rubber as well as in some cases the mechanical properties of the finished goods. In cases in which sulfur curing or vulcanization is not occurring or in which higher protein content is favored for its contribution to finished good properties, high protein composition may be selected. High ash fractions may be selected when reinforcing characteristics are desired and are exhibited by organisms like diatoms, coccolithophores, and coralline algae which are known to biologically produce minerals. These types of high mineral biomasses can aid in producing results such as higher abrasion resistance or durability and the algae can exhibit minerals with a high surface area compared to comparable mined mineral sources which can aid in foam nucleation and other characteristics not exhibited by mined minerals in addition to holding the environmental benefits ascribed to the renewable algae biomass.

Figure 1:
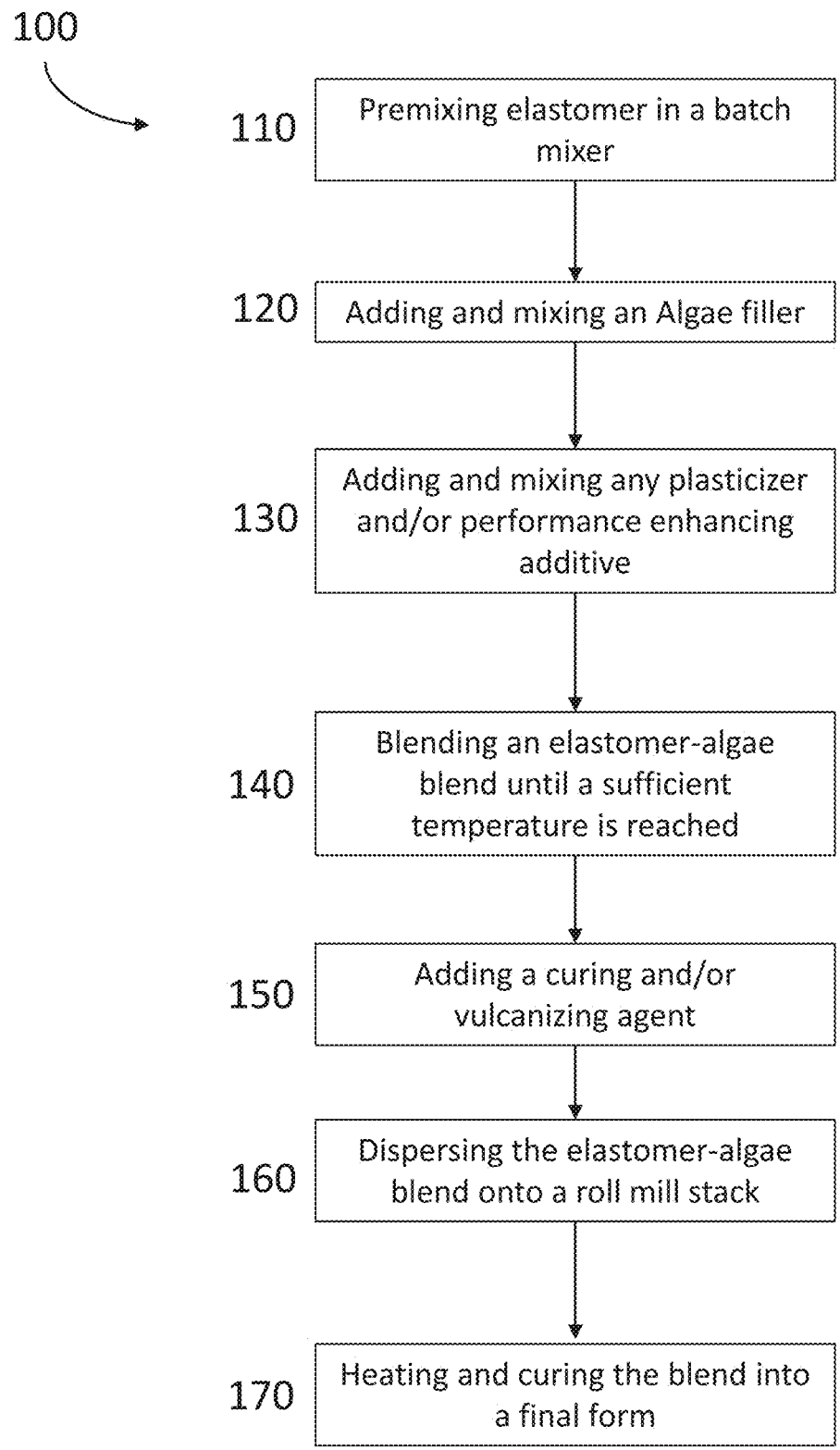
FIG. 1 is flow chart of a method of forming an elastomer-algae composite material according to the present disclosure.

Referring to FIG. 1, an example of a process 100 for producing an elastomer-algae composite material is shown. At box 110, process 100 begins by premixing an elastomer matrix in a batch mixer for a period of time sufficient to plasticize the elastomer into a suitable condition for mixing. This time can vary depending on the selection of the elastomer. In an example, the mixing time is up to about 20 minutes or more.

The process continues to box 120 where algae filler, which is formed of algae biomass and can be interchangeably referred to as algae biomass filler, is added into the batch mixer. The algae filler can be provided as particles through a milling process or the like. In some examples, the algae is processed, dried and converted to particles of a desired size to form the algae filler. Continuing to box 130, plasticizers and/or other performance enhancing additives are added to the batch mixer in sufficient amounts to deliver desired properties of the composite. At box 140, an elastomer-algae blend is formed by blending the algae and elastomer in the batch mixer to a temperature sufficient to be further mixed on a two-roll mill stack. The sufficient temperature is about 10° C. higher than the temperature sufficient for the elastomer alone.

Continuing to box 150, the process includes adding and mixing in the batch mixer a curing and/or vulcanizing agent for the elastomer. The amount of curing or vulcanizing agents are provided in an amount of about 10% to 500% more than sufficient to cure and/or vulcanize the elastomer absent the algae filler. At box 160, the process includes dispersing the elastomer-algae blend onto a two-roll mill stack. The final form is achieved in box 170 where the heating and curing of the elastomer-algae blend occurs.

Algae biomass can be prepared according to a variety of procedures to generate a suitable mixing material, referred to as the algae filler. In an example, the algae biomass can be milled such that it has a particle or material size average value of less than or equal to about 120 microns, including between about 10 and 120 microns, including 15 to 100 microns, and 20 to 80 microns. Particle size allows for easier incorporation and mixing the algae filler into an elastomer compound. Additionally, the algae biomass may be dried to below a desired moisture content such as less than 20% moisture content including less than 15% moisture as well as less than 5% moisture. In an example, the algae biomass is dried to about 3% moisture to prevent moisture from interfering with incorporation of the algae into the elastomer. The desired drying step can be performed before and/or after the filler forming step.

The term "elastomer" is understood to include, but not limited to any of the following: Natural Rubber (NR), Butadiene Rubber (BR), Acrylonitrile Butadiene Rubber (NBR), Styrene Butadiene Rubber (SBR), Hydrogenated Acrylonitrile Butadiene Rubber (HNBR), Ethylene Propylene Diene Rubber (EPDM), Chloroprene Rubber (CR), Chlorinated Polyethylene Rubber (CM), Silicone Rubber (Q), Isoprene rubbers (IR) or combinations thereof.

Once the algae biomass is sufficiently prepared as an algae filler for incorporation into an elastomer composite material, the algae filler is added in an amount ranging from about 1% to 75% including about 5% to 65% and about 10% to 55% by weight to an internal batch mixer, such as a BANBURY mixer, with an elastomer and other plasticizers or performance enhancing additives sufficient to deliver target properties of the final elastomer composite. In an example, the algae filler is added after the elastomer has been premixed for a period of time, which may extend up to about 20 minutes so that the elastomer is properly plasticized and more ready to incorporate the algae biomass filler.

Elastomer compounds with polar functionalization may be added to enhance compatibility of the algae filler to the elastomer. In an example, for NBR or SBR, a carboxylated acrylonitrile butadiene rubber (XNBR) was used and demonstrated enhanced compatibility as measured by increases in measured force exerted on an oscillating disk rheometer. In other examples, polar elastomers may be grafted with groups that have polarity like a carboxylated polar elastomer. In yet another example polar elastomers are grafted with groups including, but not limited to, acrylonitrile, styrene, or methyl methacrylate groups, or polar elastomers may have modifications to its chain such as being epoxidized or having in chain substitutions for more polar groups.

In a further example, a thermoplastic compatibilizer, which may be a grafted, a block chain substituted, or another thermoplastic polymer, which is well suited to enhance polar compatibility, may be selected to aid in compatibility between algae and the elastomer. The compatibilizers can be selected from those used for polypropylene and polyethylene and their copolymers with compatibilizers targeting these thermoplastic being effective for elastomer use. These thermoplastic compatibilizers in some cases are modified with maleic anhydride, glycidyl methacrylate, or other polar moieties. Crosslinkers or coupling agents such as isocyanates, peroxides, or glyoxal may also be used to increase the compatibility of the algae filler to the elastomer matrix. Crosslinker selection should be cautious to avoid interference with curing or vulcanization of the elastomer to prevent a loss in desired finished product properties.

Finally, the selected elastomer may have sufficient polarity to allow for adequate compatibility with algae filler and/or in some cases increasing compatibility may result in negative impacts on one or more mechanical properties of a finished product or part. Accordingly, compatibilizer usage and selection should be decided upon on the basis of the properties of the desired product targeted as well as the processing considerations of the elastomer material.

If a polar elastomer is used, it can be added during the elastomer premix to disperse and plasticize with the other elastomers before the algae biomass is introduced. The algae can then be blended with the elastomer until it reaches a temperature which is sufficient for it to be further mixed on a two-roll mill stack. Sufficient temperature can vary depending on the elastomer being used. In an example, elastomer-algae blends may need to reach a temperature of about 10° C. higher than the elastomer alone due to the impact of the algae biomass on the viscosity of the elastomer.

Outside of compatibilizers various process and performance enhancing aids may be added to an algae elastomer foam to enhance the physical properties and/or processability of the algae-elastomer blend. These may include waxes, oils, plasticizers, thermoplastics, mineral fillers, bio-fillers, pigments, accelerators, antioxidants, flame retardants, and surfactants/wetting agents. Selection and usage of these processing or performance enhancing aids can be done by one skilled in the art of finished rubber goods manufacturing based on the needs of the product.

Once the elastomer-algae blend has been sufficiently mixed, it can be further dispersed by running through a two mill roll stack and being folded over onto itself. After being sufficiently dispersed through layering on the two-mill roll stack, the elastomer-algae blend can be stored until ready for use. Prior to storage the algae-elastomer composite may be added to a single screw extruder and extruded through a die and pelletized in order to make packaging, handling or storage easier.

An algae elastomer batch may also be loaded with more algae filler than the quantity of algae desired in a finished good such that an algae elastomer composite masterbatch is created. A masterbatch may be useful in allowing the composite to be made and used in different locations without incurring as significant shipping and environmental drawbacks and it is also useful in serving the needs of many products at once if they are sufficiently similar that the their final formulations can be achieved in the mixing step before use allowing masterbatches to be made with greater economies of scale in production. A masterbatch in most cases will have greater algae contents than is intended in an end or finished product since it is intended to be let down and, in an example, includes up to 75% algae content by weight including up to 60% algae content by weight and up to 40% algae content by weight. In yet a further example, the algae content of the masterbatch is between 1% and 75% by weight including 10% to 75% by weight. In addition, in certain cases a thermoplastic may be blended with algae to create a masterbatch which can be let down into the elastomer blend. Thermoplastic masterbatches can have the advantages of being made on extruders which can have improved mixing and run continuously, however, thermoplastics do not exhibit the same properties as elastomers, and therefore in many cases a loss of properties will result when using thermoplastic masterbatches.

While Banbury mixers and two mill roll stack mixing is the most common route to mix and disperse materials in elastomer manufacturing any mixer which is suitable for plasticizing the elastomer and introducing and dispersing a powder in the elastomer may be used. This may include but is not limited to single extruders, twin screw extruders and other mixing equipment used in processing rubbers.

When ready for production, the elastomer-algae blend (masterbatch) is added back into an internal batch mixer to introduce curing and vulcanizing agents for the elastomer. Due to interference with these agents from the algae, it is typical to see relatively higher doses of these agents being added to achieve a desired result. In an example, 10% to 500%, including 25 to 300% and 50 to 200% more of these agents will allow curing and/or vulcanizing to occur as desired. If an elastomer algae masterbatch is being used, in addition to vulcanizing and curing agents, more elastomer material will likely be added in a mixing step before the product is used. This mixing step may be the same as the step introducing curing and vulcanizing agents or it may be conducted as a separate step.

After mixing is finished, the elastomer-algae blend is further dispersed on the two-roll mill stack through folding the material over onto itself and layering it. The two-roll milling process often requires around 10° C. higher temperatures to properly disperse the material due to the viscosity changing effects of the algae with the degree of temperature change required depending on the amount of algae present.

After the two-roll mill stack, the elastomer-algae blend is ready to be heated and cured into a finished part or end product. The heating and curing process may take many forms. For example, in one form, an extruder may heat, mix, and extrude the material and then it may be passed through a heating tunnel in which it is cured and foamed into an elastomer-algae composite foam sheet. In yet another form, the resulting elastomer-algae composite may be rolled into flat sheets and then applied to molds where it is pressed into a form and then heated and cured into a desired finished product, such as a shoe outsole or other shoe component. The elastomer-algae blend material can be shaped and heated in the final processing step to generate the desired form to service a desired market using conventional processing methods. In some examples, little to no modifications to the conventional processing conditions are needed.

The present disclosure further provides for an elastomer foam material that includes algae. In the example of an elastomer foam such as that which might be used in insulation, gasket and seals, sound abatement, anti-fatigue mats and other applications, the addition of a foaming agent and in some cases, accelerants are used to produce the foam. The foaming agents and accelerants are added along with the curing and vulcanizing agents in the last mixing step via an internal batch mixer so as to ensure there is no early evolution of gas from the rubber material. Foaming agents and accelerants are added so as to yield the appropriate degree of foaming and have the foaming onset occur after sufficient curing has occurred in the material to allow for gas entrapment.

Accelerant loading and temperatures required to foam will depend on the elastomer being foamed, but the addition of algae can in some cases cause higher temps to be reached for proper curing before foaming onset should occur. This phenomenon can be offset to some degree through the use of compatibilizers and the proper loading of curing agents and accelerants to balance between curing rate and foaming rate. Foaming agent selection and loading depends on the elastomer being used and the desired properties of the foam, however, in at least some cases, foaming agents make up 1 to 30% of the formula including 2 to 25% and 5 to 20% by weight. The algae can serve as a nucleating agent for bubble formation especially mineralized algae, but additional nucleating agents may be used if desired. Additional algae in a rubber foam may create an open cell structure which is beneficial in some circumstance so long as it does not create a loss in desired properties such as compression. Additionally, the incorporation of low levels of algae into elastomer foam goods has been shown to improve compression set properties which is a critical property in foam performance.

In an example of a solid rubber good such as might be found in shoe soles, grips, automotive parts, hosing, tires, and other products, algae-elastomer blends can be used using conventional compression molding processing techniques. The algae-elastomer blends can rolled flat into sheets or be cut or otherwise shaped into pre-forms, which are then placed in molds, which are then closed and subjected to sufficient heat and pressure to cure the rubber and form a finished part or good. When algae is present, longer times spent curing in the molds may be desired, but are not required if performance requirements are met without longer cure times.

Similar techniques may be used for transfer molding. Injection molding of elastomers and calendaring of elastomers are also envisioned with standard industry techniques being suitable for the algae elastomer blends of the present disclosure, and only minor condition changes being necessary to produce finished parts or goods which meet industry expectations. These condition changes will likely attempt to address the viscosity changes and cure time and temp changes that the use of algae in rubber introduces.

In solid elastomer goods, algae has been shown to reinforce the elastomer finished goods contributing to significant improvement in structural characteristics and measures of toughness such as tear strength. Non-mechanical benefits may exist in some cases due to increases in surface polarity and Gibbs free energy which can affect the finished goods interactions with solvents, adhesives, grip characteristics, and other unique benefits.

Figures 2A, 2B:
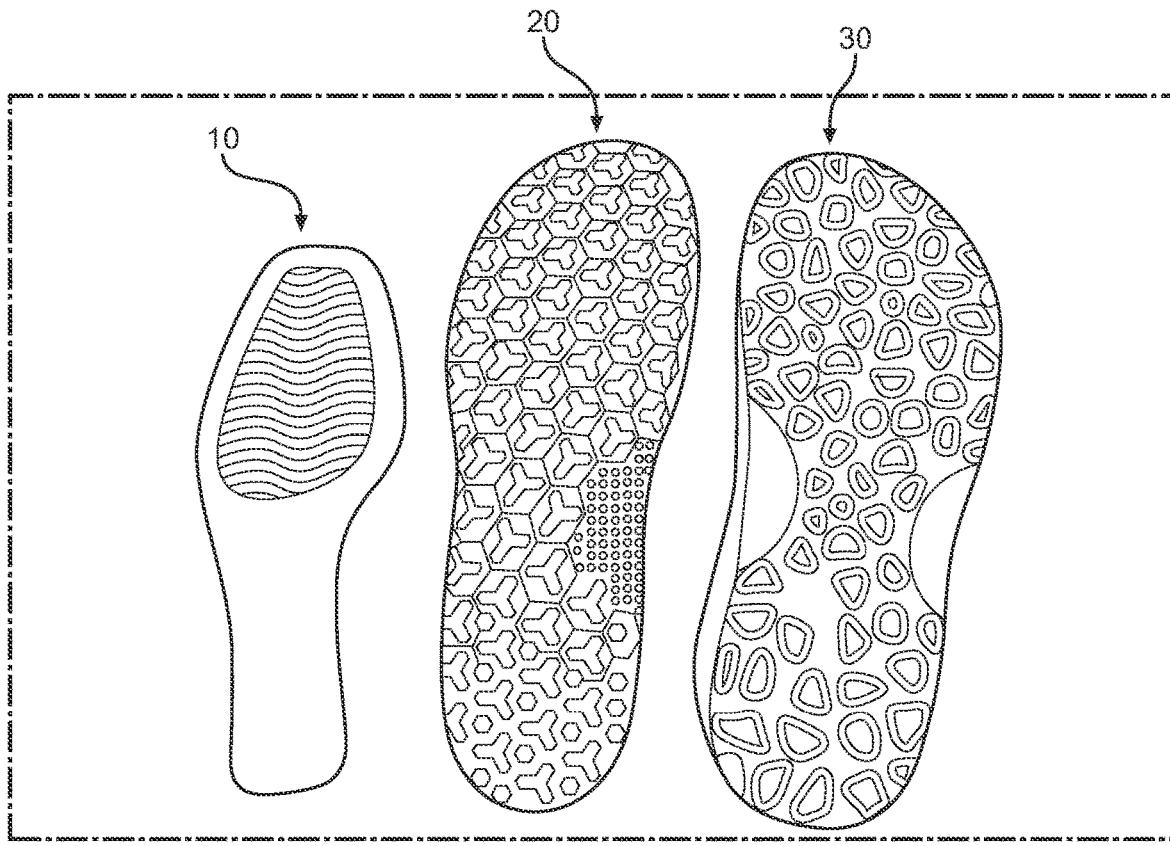
FIG. 2A is a photograph a final product including an elastomer-algae composite material of the present disclosure and produced according to the method of the present disclosure.
FIG. 2B is a chart of physical properties of final product 10 of FIG. 2A.

Referring to the examples of FIGS. 2A, 2B, 2C and 2D, a plurality of shoe components (10, 20, and 30) is shown and formed according to a method of the present disclosure. These examples show a solid elastomer algae composite material. The shoe components include a first shoe component 10 of a relatively thinner smaller size. In this example, component 10 can be an insole or midsole. Shoe component 20 is a larger shoe component as compared to component 10 and includes a textured bottom surface which can be used as an outsole. Shoe component 30 is still larger relative to shoe components 10 and 20 and also serves as an outsole with a textured bottom like outsole component 20. All three components include an elastomer-algae composite material of the present disclosure. A chart illustrating resulting properties of component 10 is shown in FIG. 2B to illustrate that a 15% algae content by weight is feasible in an elastomer composite. In this example, the component included a masterbatch which includes both algae and thermoplastic. Shoe components 10, 20 and 30 exhibit certain desired results of properties including tear, specific gravity (SG), split tear, and abrasion strength along with hardness and elongation data. FIG. 2C illustrates a chart of test results for component 30 to identify properties of the component. FIG. 2D shows a comparison table of a 10% algae elastomer composite against a 5% algae elastomer composite. In this example, the dry slip and wet slip characteristics will be impacted by the shape, size, and texture of the final end product. Moreover, using an elastomer-algae composite product has important environmental benefits and reduces the reliance on fossil fuels.

Figure 3:
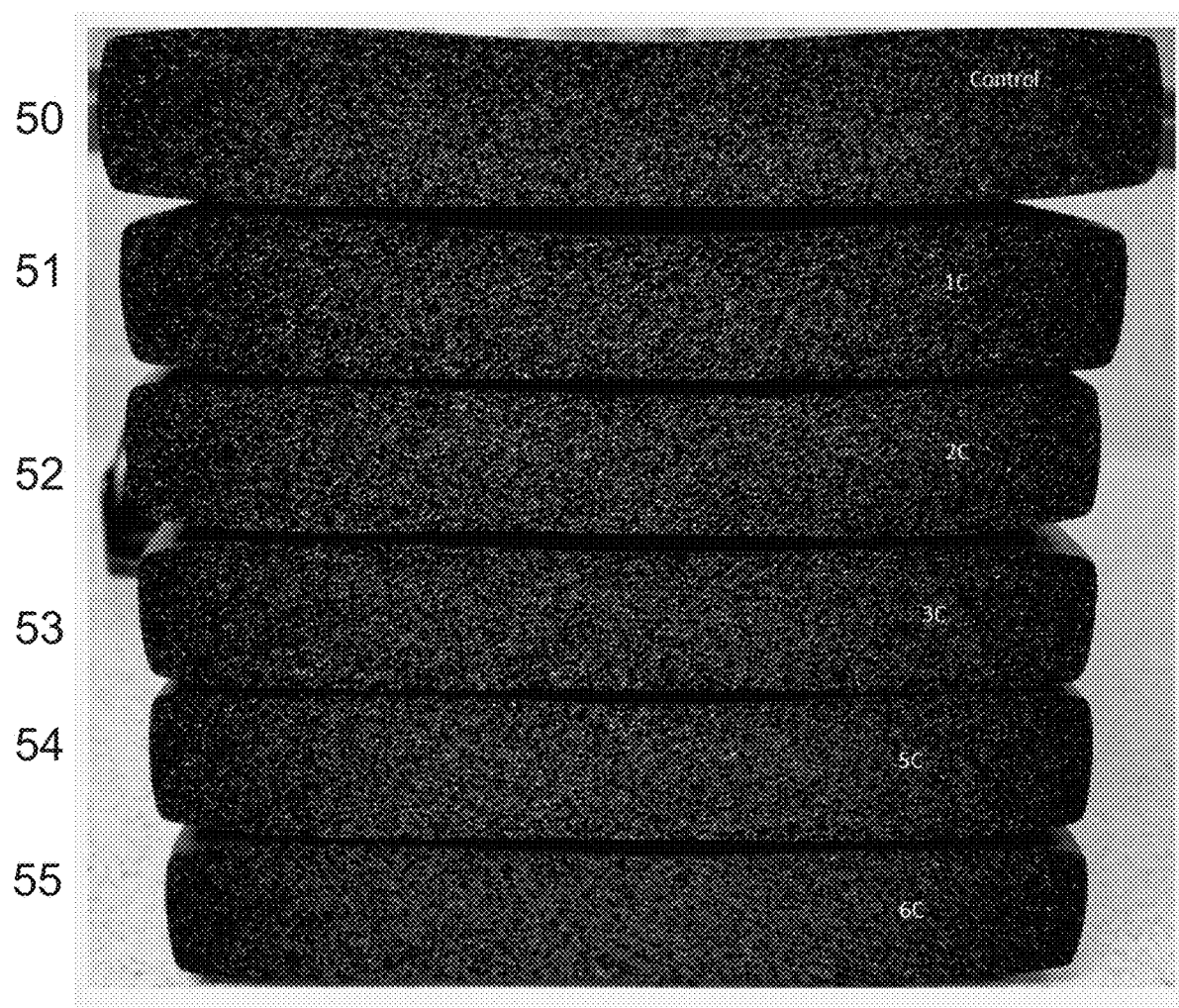
FIG. 3 is a photograph of a plurality of experimental elastomer-algae composite materials produced according to a method of the present disclosure.
Figure 4:
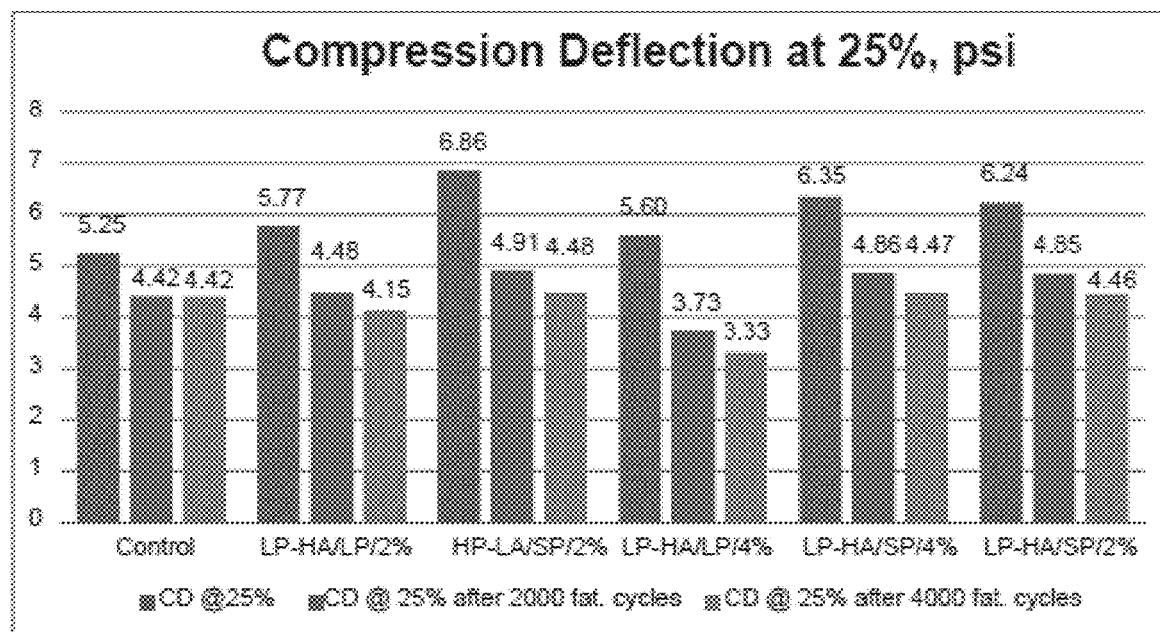
FIG. 4 illustrates charts showing compression testing and percent change after fatigue testing of the materials of FIG. 3.
Figure 4:
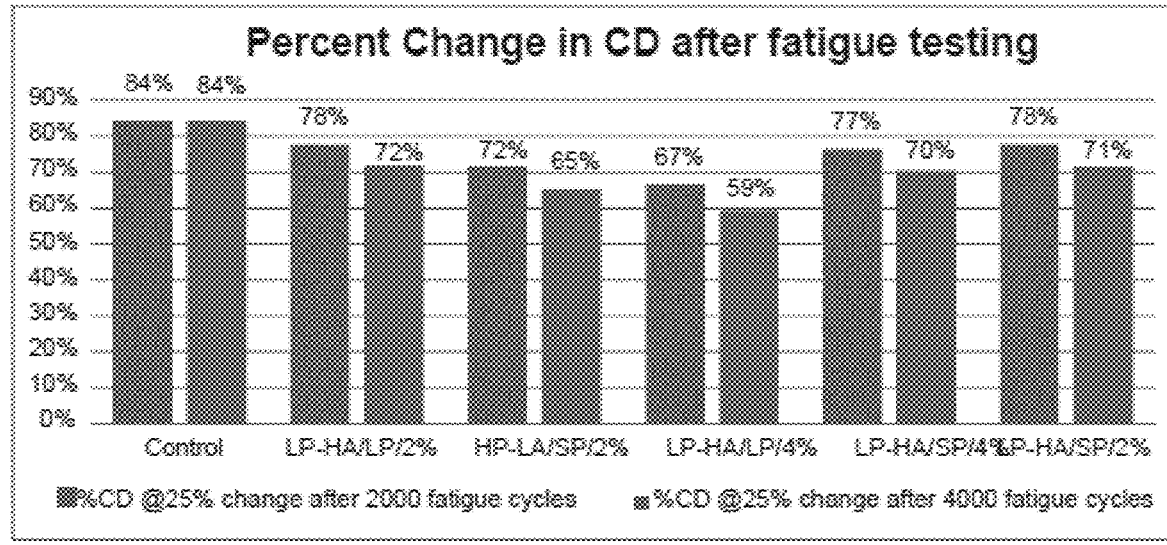
Figure 5:
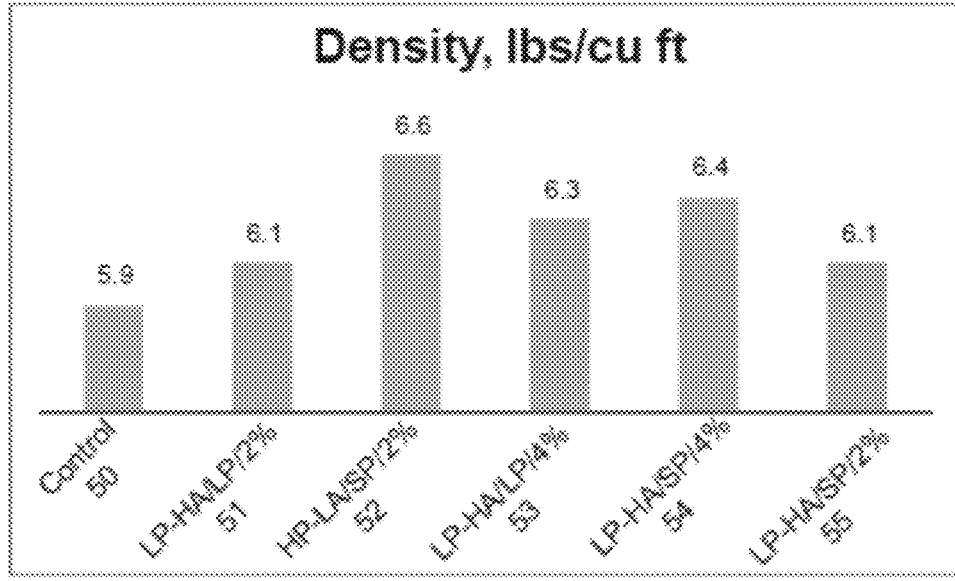
FIG. 5 illustrates charts showing density and thickness of the materials of FIG. 3.
Figure 5:
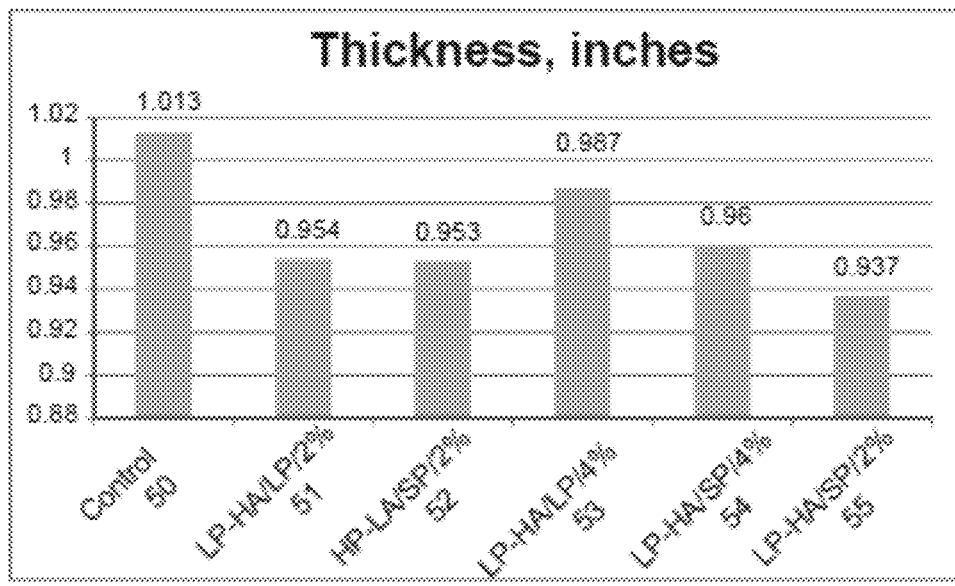

FIGS. 3-5 illustrate a control elastomer foam sample 50 that includes elastomer without algae, and example elastomer-algae foam composite materials 51, 52, 53, 54, and 55, produced according to the present disclosure. These materials were labeled and tested and shown in a stack in FIG. 3. A control sample 50, is shown positioned on top of a stack that includes samples 51, 52, 53, 54, and 55. These samples were used to illustrate that the various algae containing materials resulted in close to equal, equal, and/or improved physical properties, particularly related to compression deflection at 25% psi and after 2000 and 4000 fatigue cycles. In these examples, the control sample 50 includes elastomer with no algae. Sample 51 through 55 are from a factorial design experiment looking at particle size, protein to mineral ratio, and compatibilizer loading to establish best conditions for desired foam properties. Large particles had an average particle size of around 70-80 micron and small particle samples had an average particle size of around 25-35 micron. The labeling of the components are defined as: LP-HA/LP=Low Protein, High Ash, Large Particles; HP-LA/SP=High Protein, Low Ash, Small Particles; LP-HA/SP=Low Protein, and High Ash, Small Particles. The percentage relates to compatibilizer loading. Sample 51 includes LP-HA/LP/2%, sample 52 includes HP-LA/SP/2%, sample 53 includes LP-HA/LP/4%, sample 54 includes LP-HA/SP/4%, and sample 55 includes LP-HA/SP/2%. Moreover, the percentage change after fatigue testing also was reduced for algae containing materials as shown in FIG. 4. FIG. 5 illustrates how density can be increased while reducing thickness as compared to the control state 50. Up to 20% algae content has been demonstrated in similar foams to those shown in the figures.

It should be noted that the steps described in the method of use can be carried out in many different orders according to user preference. The use of "step of" should not be interpreted as "step for", in the claims herein and is not intended to invoke the provisions of 35 U.S.C. § 112 (f). Upon reading this specification, it should be appreciated that, under appropriate circumstances, considering such issues as design preference, user preferences, marketing preferences, cost, structural requirements, available materials, technological advances, etc., other methods of use arrangements such as, for example, different orders within above-mentioned list, elimination or addition of certain steps, including or excluding certain maintenance steps, etc., may be sufficient.

The embodiments of the disclosure described herein are exemplary and numerous modifications, variations and rearrangements can be readily envisioned to achieve substantially equivalent results, all of which are intended to be embraced within the spirit and scope of the disclosure. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is:

1. A algae-elastomer composite comprising:
    (a) an elastomer matrix;
    (b) a biomass reinforcement distributed through the elastomer matrix, wherein the biomass comprises algae and the algae biomass includes protein, ash, carbohydrate, and lipids when distributed into the elastomer matrix; and
    (c) a mixing additive selected from the group consisting of a plasticizer, a compatibilizer, a vulcanizing agent, a curing agent, a crosslinker, a coupling agent, an elastomer compound having polar functionalization, a thermoplastic compound having polar functionalization, a performance enhancing additive, and combinations thereof, wherein the mixing additive is sufficient to achieve a desired property.

2. The composite of claim 1, wherein the algae is present in a milled condition having a mean particle size value of up to 120 microns.

3. The composite of claim 1, wherein the algae is mixed with the elastomer matrix in a dry condition having a moisture content of below about 20%.

4. The composite of claim 3, wherein the algae is mixed with the elastomer matrix in a dry condition having a moisture content of below about 3%.

5. The composite of claim 1, wherein the elastomer matrix is selected from the group consisting of natural rubber (NR), butadiene rubber (BR), acrylonitrile butadiene rubber (NBR), styrene butadiene rubber (SBR), hydrogenated acrylonitrile butadiene rubber (HNBR), ethylene propylene diene rubber (EPDM), chloroprene rubber (CR), chlorinated polyethylene rubber (CM), silicone rubber (Q), and combinations thereof.

6. The composite of claim 1, wherein the algae is present in an amount between about 1% to 75% by weight of composite.

7. The composite of claim 1, wherein the algae is selected from the group of algae species consisting of Haptophyta, Cyanophyta, Chlorophyta, Ochrophyta, Rhodophyta, Phaeophyta and combinations thereof.

8. The composite of claim 1, wherein the protein, ash, carbohydrate, and lipids in the algae biomass are present by weight at a composition of protein from about 1% to 60%, ash from about 1% to 90%, carbohydrate from about 1% to 50%, and lipid from about 1% to 30%.

9. The composite of claim 1, wherein the elastomer is present in a premixed condition resulting in a plasticized state.

10. The composite of claim 1, wherein the mixing additive is either the elastomer compound having polar functionalization or the thermoplastic compound having polar functionalization and comprises a functionalizing agent selected from the group consisting of a carboxylate, styrene, methyl methacrylate, acrylonitrile, glycidyl methacrylate, maleic anhydride, epoxide, and combinations thereof.

11. The composite of claim 1, wherein the mixing additive is a coupling agent or a compatibilizer having at least one member selected from the group consisting of isocyanate, peroxide, glyoxal coupling agents, and combinations thereof.

12. The composite of claim 1, wherein the additive is present in a premixed condition with the elastomer matrix.

13. The composite of claim 1, wherein the algae is present in a milled condition having a mean particle size value of between 15 and 100 microns.

14. The composite of claim 1, wherein the algae is present in a milled condition having a mean particle size value of between 20 and 80 microns.

15. The composite of claim 1, wherein the mixing additive is an elastomer compound having polar functionalization comprising carboxylated acrylonitrile butadiene rubber (XNBR).

16. A shoe component comprising:
    an algae elastomer composite including (i) an elastomer matrix, (ii) a biomass reinforcement distributed through the elastomer matrix, wherein the biomass comprises algae and the algae biomass includes protein, ash, carbohydrate, and lipids when distributed into the elastomer matrix; and (iii) a mixing additive selected from the group consisting of a plasticizer, a compatibilizer, a vulcanizing agent, a curing agent, a crosslinker, a coupling agent, an elastomer compound having polar functionalization, a thermoplastic compound having polar functionalization, a performance enhancing additive, and combinations thereof, wherein the mixing additive is sufficient to achieve a desired property;

wherein the shoe component is selected from the group consisting of an outsole, midsole, insole and combinations thereof.

\* \* \* \* \*